(12) United States Patent
Nitta et al.

(10) Patent No.: US 6,849,655 B2
(45) Date of Patent: Feb. 1, 2005

(54) AQUEOUS LIQUID FORMULATIONS

(75) Inventors: Hiroo Nitta, Osaka (JP); Takayuki Nagao, Osaka (JP)

(73) Assignee: Kissei Pharmaceutical Co., Ltd., Nagano-Ken (JP)

( * ) Notice: Subject to any disclaimer, the term of this patent is extended or adjusted under 35 U.S.C. 154(b) by 0 days.

(21) Appl. No.: 10/276,511

(22) PCT Filed: May 14, 2001

(86) PCT No.: PCT/JP01/03976
§ 371 (c)(1),
(2), (4) Date: Feb. 19, 2003

(87) PCT Pub. No.: WO01/87298
PCT Pub. Date: Nov. 22, 2001

(65) Prior Publication Data
US 2003/0166705 A1 Sep. 4, 2003

(30) Foreign Application Priority Data
May 15, 2000 (JP) ........................... 2000-141622

(51) Int. Cl.$^7$ ................... A01N 43/38; A61K 31/40
(52) U.S. Cl. ..................................... 514/416; 514/419
(58) Field of Search ........................ 514/416, 419

(56) References Cited

U.S. PATENT DOCUMENTS 5,202,331 A * 4/1993 Tomoi .......................... 514/277
5,290,774 A 3/1994 Morita et al.

FOREIGN PATENT DOCUMENTS

| EP | 0 298 192 | 1/1989 |
|----|-----------|--------|
| EP | 0 436 726 | 7/1991 |
| EP | 1 057 813 | 12/2000 |
| JP | 7-23302 | 3/1995 |
| JP | 07330726 | * 12/1995 |
| JP | 10-25254 | 1/1998 |
| JP | 10-29937 | 2/1998 |
| WO | WO 91/01718 | 2/1991 |
| WO | WO 97/24129 | 7/1997 |
| WO | WO 99/43652 | 9/1999 |

* cited by examiner

Primary Examiner—Alton N. Pryor
(74) Attorney, Agent, or Firm—Merchant & Gould P.C.

(57) ABSTRACT

An aqueous liquid formulation which comprises a compound of formula I:

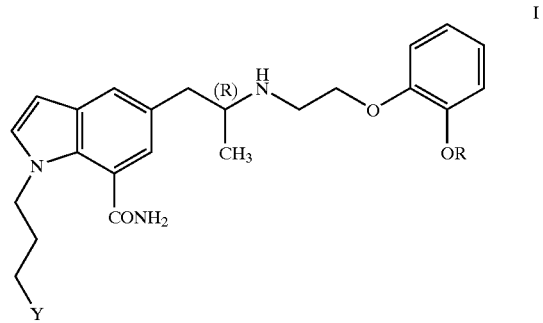

wherein Y is a hydroxy group, a carboxyl group, an acyloxy group or an alkoxycarbonyl group; R is a lower alkyl group or a lower alkyl group with one or more halogen atoms; or a pharmaceutically acceptable salt thereof or a pharmaceutically acceptable solvate of them as an active ingredient, together with one or more substances selected from the group consisting of boric acid, borax, phosphate salts and carbonate salts.

7 Claims, No Drawings

AQUEOUS LIQUID FORMULATIONS

TECHNICAL FIELD

The present invention relates to an aqueous liquid formulation comprising an indole derivative as an active ingredient, and specifically, it relates to an aqueous liquid formulation comprising an indole derivative with an enhanced photostability.

BACKGROUND OF THE INVENTION

In order that a pharmaceutical product can exert an intended effect, the activity of the pharmaceutical product should essentially be retained sufficiently at all of the steps of the handling of raw pharmaceutical chemicals, the blending, the filling, and the packaging, as well as during the period from the distribution to the termination of the use by patients. Not a few of compounds used as active ingredients are unstable against light and heat. Generally, the decomposition mechanism varies depending on the causative factors and the entity of the compounds, and is complicated. Therefore, it is very difficult to thoroughly elucidate such complicated mechanism so that the compound itself is modified for stabilization. Because photodecomposition in particular is involved in the specific property of a compound in absorptivity of a light, it is extremely difficult to modify the specific property while retaining an intended activity thereof. In such case that a compound that is unstable against light is used as an active ingredient, it should be necessary to design formulations to stabilize the compound.

Solution is affected prominently by light, and liquid formulations such as eye drops and injections should be protected from exposure to light. In eye drops, which are directly applied to mucosa, not only the decomposition of an active ingredient causes the reduction or elimination of medicinal efficacy following the decrease of the content, but also the resulting decomposed products may cause serious safety concerns on living biological organisms.

Measures to block the decomposition of ingredients unstable against light by formulation design include a method comprising using colored containers or labels or shielded bags, and a method comprising adding appropriate stabilizers to the formulations. However, the former method cannot essentially provide complete shielding and, additionally, the method cannot sufficiently protect the ingredients from exposure to light during the steps prior to the filling or during the period of the use by patients. Further, the Japanese Pharmacopoeia defines in the General Rules for Preparations that eye drops should not contain any insoluble particulate matters readily detectable with naked eye, and this definition is also applicable to injections. Because the appropriateness of eye drops or injections as pharmaceutical formulations is examined by visual inspection, the use of colored light-shielded containers which might affect the test of insoluble particulate matters should be limited.

On the other hand, it is difficult to determine the optimal conditions for stabilizers to block the decompositions because the photodecomposition mechanism is complicated and varies on the entity of ingredient. Additionally, the influences of the stabilizer on tissues should also be considered. For example, Japanese Patent Publication (kokoku) No. 23302/1995 describes a method for stabilizing an eye drop containing a drug unstable against light, which comprises incorporating boric acid and/or borax as well as polyhydric alcohol into the eye drop. Polyhydric alcohols, however, raise the viscosity of eye drops to increase the retention of the drug in eye mucosa, and enhance the irritation of the drug if the drug exhibits even a slight irritation. Eye irritation will also potentially induce the increase of lacrima amount to dilute active ingredients therein, thus resulting in no attainment of the intended effect.

Additionally, Japanese Patent Publication (kokai) No. 16724/1989 discloses an injection of vinca alkaloid of a dimer indole-dihydroindole compound. It is described therein that an injection prepared by dissolving the vinca dimer in a solution of EDTA, a preservative and acetate buffer, is stable in darkness at ambient temperature for nine months.

DISCLOSURE OF THE INVENTION

As shown in the above examples, indole derivatives are generally so unstable against light that it is frequently required to store the derivatives in darkness. However, it is practically impossible to continue the storage of aqueous liquid formulations of multi-dose type such as eye drops, in darkness, since these formulations are liable to exposure to light on usage. Additionally, the storage and application conditions are not constant among these formulations, since they are applied in small portions by individual patients themselves over a long period of time. Under the circumstances, it is desired to develop a pharmaceutical formulation stable against light.

Eye drops require no eye irritation in addition to the stability of active ingredients and the stability of the formulation. Thus, the use of acetate buffer is limited because of its topical irritation. The problems are serious particularly for eye drops to be administered continuously for a long term, such as eye drops for treating glaucoma, and make the design of eye drop formulations tough.

In common to general pharmaceutical products, additionally, components to be contained in pharmaceutical formulations except for active ingredients should be the required minimum. Thus, it is desired to develop a method for attaining a maximum photostability while limiting the number and quantities of the components to the minimum.

It has been known that indole derivatives substituted through a secondary amine with catechol derivatives include compounds having an intraocular tension-reducing action, which are useful as prophylactic or therapeutic agents of glaucoma or diseases with high intraocular tension (WO 99/43652). Concerning the stability of such indole derivatives, the publication describes that the indole derivatives are stable in acetate buffer, pH 5.0, under storage in darkness, but never describes anything about the photostability.

The present inventors have made investigations about these indole derivatives and have found that the problems over the instability thereof in aqueous solutions against light involving possible eye irritation should preliminarily be overcome in advance of clinical application of the derivatives.

The invention provides an aqueous liquid formulation which comprises a compound of formula I:

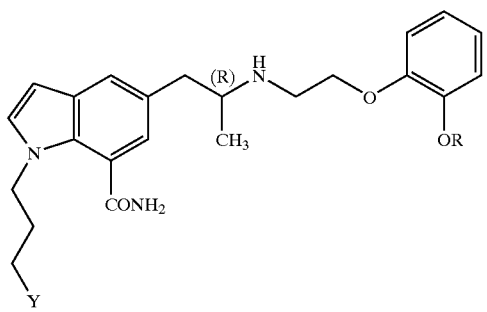

wherein Y is a hydroxy group, a carboxyl group, an acyloxy group or an alkoxycarbonyl group; R is a lower alkyl group or a lower alkyl group with one or more halogen atoms), or a pharmaceutically acceptable salt thereof or a pharmaceutically acceptable solvate of them, as an active ingredient, and concurrently comprises one or more substances selected from the group consisting of boric acid, borax, phosphate salts and carbonate salts.

BEST MODE FOR CARRYING OUT THE INVENTION

In the present specification, "a compound of formula I, or a pharmaceutically acceptable salt or a pharmaceutically acceptable solvate of them" as an active ingredient of the aqueous liquid formulation of the present invention may also be simply referred to as "indole derivative I".

As shown in Test Example hereinafter, the formulations of the present application make it possible to inhibit the photo-decomposition of indole derivative I as an active ingredient therein, and therefore the formulations of the present invention are clinically useful formulations, which can exert safe and excellent therapeutic effects for a long period of time.

The aqueous liquid formulations of the present invention are useful as an injection or an eye drop since the formulations avoid any concern about the retention of active ingredients having topical irritation in ocular mucosa. Particularly, the avoidance of any concern about eye irritation is very advantageous to ensure patient compliance and, additionally, it serves to prevent active ingredients from dilution with the increase in lacrima amount due to irritation, suggesting that the formulations are very useful as an eye drop. The aqueous liquid formulation of the present invention can also maintain the quality of active ingredients in a stable manner for a long term, suggesting that the formulations are useful as a therapeutic or prophylactic eye drop for ocular diseases requiring long-term therapy.

The aqueous liquid formulations of the present invention preferably comprises indole derivative I and one or more substances selected from the group consisting of boric acid, borax, phosphate salts and carbonate salts.

Further, the present invention provides a process for preparing an aqueous liquid formulation, which comprises blending indole derivative I with one or more substances selected from the group consisting of boric acid, borax, phosphate salts and carbonate salts at concentrations effective for the photostabilization of indole derivative I.

Still further, the present invention provides a method for photostabilizing an active ingredient in an aqueous liquid formulation, wherein the active ingredient is indole derivative I or a pharmaceutically acceptable salt thereof or a pharmaceutically acceptable solvate of them, which comprises incorporating into the formulation one or more substances selected from the group consisting of boric acid, borax, phosphate salts and carbonate salts at concentrations effective for the photostabilization of the active ingredient.

As the effective ingredient of the aqueous fluid of the present invention, an appropriate one selected from indole derivative I as defined above may be used. For the purpose of the present invention, Y in formula I is preferably a hydroxy group or an acyloxy group, and more preferably a hydroxy group or a pivaloyloxy group. Additionally, R is preferably a methyl group, an ethyl group, a propyl group, an isopropyl group and a trifluoroethyl group, and more preferably an ethyl group or a trifluoroethyl group. Specific examples of preferable compounds include the following four types of compounds, pharmaceutically acceptable salts thereof, or pharmaceutically acceptable solvates of them.

TABLE 1

| Formula I | R | Y |
|---|---|---|
| Compound 1 | ethyl group | pivaloyloxy group |
| Compound 2 | 2,2,2-trifluoroethyl group | pivaloyloxy group |
| Compound 3 | ethyl group | hydroxy group |
| Compound 4 | 2,2,2-trifluoroethyl group | hydroxy group |

It has been known that these compounds have excellent $\alpha_1$-adrenoceptor blocking actions and that compounds 1 and 2 in particular are highly cornea-permeable and useful as therapeutic agents of glaucoma or diseases with high intraocular tension (WO 99/43652). Preparations of the compounds are described in the publication.

All the compounds are suitable as an active ingredient of the pharmaceutical formulation of the present invention and compounds 1 and 2 are preferable.

The asymmetric carbon atom marked with (R) in formula I can be in (R)-configuration and a mixed form of (R)-configuration and (s)-configuration. In the formulations of the present invention, either the (R)-form optically resolved or a mixture of (R)-form with (s)-form can be used, and the (R)-form optionally resolved is preferable for ophthalmology.

Salts of the compound of formula I may include, but is not limited to, pharmaceutically acceptable salts with organic or inorganic acids. For example, the salts include acid addition salts with mineral acids such as hydrochloric acid, hydrobromic acid, hydroiodic acid, sulfuric acid, nitric acid and phosphoric acid; and organic acids such as carbonic acid, formic acid, acetic acid, propionic acid, butyric acid, oxalic acid, citric acid, succinic acid, tartaric acid, fumaric acid, malonic acid, maleic acid, malic acid, lactic acid, adipic acid, benzoic acid, salicylic acid, methanesulfonic acid, benzenesulfonic acid, p-toluenesulfonic acid, glutamic acid and aspartic acid.

The pharmaceutically acceptable solvates include for example hydrate or solvates with pharmaceutical acceptable solvents such as ethyl alcohol.

To prepare the aqueous liquid formulation of the present invention, one or more selected from the group consisting of boric acid, borax, phosphates and carbonates may be blended. In the present specification, these substances may be referred to as "photostabilizers" for convenience. The photo-stabilizers for indole derivative I (for example, compounds 1 to 4, or salts or solvates thereof) are pharmaceutically acceptable in the ophthalmology field. The photostabilizers exude no odor unlikely acetate buffer, and never gives unpleasant feeling during eye drop application, showing that the photostabilizers are very useful for allowing the clinical application of derivative I for the purpose of therapeutic treatment of diseases with high intraocular tension and glaucoma.

In case that the aqueous liquid formulation of the present invention is an eye drop, the photostabilizer therefor is preferably boric acid, borax and phosphate salts, and more preferably boric acid and/or borax. Owing to the preservative action of boric acid and/or borax, boric acid or borax can reduce the risk of contamination of multi-dose type eye drops during a long term of use. Because the amount of antiseptics or preservatives to be blended therein can be reduced, the cytotoxicity of the formulation can be attenuated. Thus, the formulation is suitable as an aqueous liquid formulation for the therapeutic treatment or prophylaxis of diseases with high intraocular tension and glaucoma requiring long-term dosing.

The concentration of the photostabilizer in the aqueous liquid formulation varies, depending on the purpose of the use and the combination of individual photostabilizers. The concentration can be determined appropriately within the concentration range acceptable in the pharmaceutical field. The amount of the photostabilizer such as boric acid, borax, phosphate salts and carbonate salts to be blended in the formulation of the present invention can be determined in view of the concentration (quantity) thereof required to adjust the pH to the range of 4 to 8, preferably the range of 5 to 7.

In order to improve the photostability of indole derivative I, boric acid may be contained at 0.01 to 5.6 w/v %, preferably within the range of 0.5 to 3.0 w/v %; and borax may be contained at 0.01 to 5 w/v %, preferably 0.01 to 1 w/v %.

Any pharmacologically acceptable phosphate salt may be contained, including for example primary phosphate salts and secondary phosphate salts, and specifically sodium mono-hydrogen phosphate, sodium dihydrogen phosphate, potassium monohydrogen phosphate, potassium dihydrogen phosphate, sodium ammonium hydrogen phosphate, diammonium hydrogen phosphate, and ammonium dihydrogen phosphate. The concentration of the phosphate salt in the pharmaceutical formulation is within the range of 0.01 to 5 w/v %, and preferably within the range of 0.5 to 3.0 w/v %.

Carbonate salts include potassium carbonate, potassium hydrogen carbonate, sodium hydrogen carbonate, and sodium carbonate. The concentration of the carbonate salt in the pharmaceutical formulation is within the range of 0.01 to 5 w/v %, and preferably within the range of 0.01 to 3 w/v %.

The aqueous liquid formulation of the present invention which contains these photostabilizers within the concentration range as mentioned above (also referred to as photo-stabilizing concentration), can prevent the photodecomposition of indole derivative I, to retain the activity thereof. Additionally, the aqueous liquid formulation exhibits neither topical irritation nor interaction with packaging containers, showing that the formulation is safe and clinically useful. Owing to no irritation on ocular mucosa, the formulation is superior as eye drop.

Two or more photostabilizers may appropriately be used in combination under the conditions that the resulting formulation has physico-chemical properties (pH, osmotic pressure ratio, viscosity) acceptable for eye drops and injections. The effective concentration of the components varies depending on the types of the ingredients in combination and the blend ratio. Principally, the concentration should be determined on the basis of the photostabilizing concentration of each component. Generally, the total concentration of the component may be 0.01 to 10.6 w/v %, preferably 0.01 to 8.0 w/v % and more preferably 0.01 to 4.0 w/v %, for more stable solubility.

Generally, the pH is appropriately determined within the pH range acceptable for aqueous liquid formulations such as eye drops and injections. Because the compound of formula I is likely to dissolve at acidity in a more stable fashion, pH 4 to 8 is preferable and pH 5 to 7 is more preferable.

The aqueous liquid formulation of the present invention may contain appropriately isotonic agents, pH adjusting agents, antiseptics or preservatives, thickeners, auxiliary solubilizing agents, typical stabilizers, chelating agents, solubilizing agents and other useful components, all of which are commonly used in the art, as long as the aim of the present invention can be attained.

Isotonic agents include for example potassium chloride, calcium chloride, sodium chloride, glycerin, D-mannitol, aminoethylsulfonic acid, and glucose. PH adjusting agents include for example hydrochloric acid, dilute hydrochloric acid, glacial acetic acid and sodium hydroxide. Antiseptics or preservatives include for example benzalkonium chloride, benzalkonium chloride with an alkyl group having 12 carbon atoms, benzethonium chloride, chlorhexidine gluconate, chlorobutanol, sorbic acid, potassium sorbate, methyl parahydroxybenzoate, ethyl parahydroxybenzoate, propyl parahydroxybenzoate, butyl parahydroxybenzoate, Polyquad (polyquartenium-1), Dymed (polyaminopropyl biguanide), alkylaminoethylglycine hydrochloride, cetylpyridinium chloride, and thimerosal. Thickeners include for example dextran, hydroxyethylcellulose, hydroxycellulose, carboxymethylcellulose, Carbopol, hydroxypropylmethylcellulose, polyvinyl alcohol, polyvinylpyrrolidone, methylcellulose, sodium chondroitin sulfate, agarose, tragacanth, and gum xanthan. Auxiliary solubilizing agents include for example urea, ethanol, propylene glycol, polyoxyethylene-hardened castor oil 60, polyoxyethylene castor oil, polyoxyl 40 stearate, polysorbate 80, macrogol 4000, and monoethanolamine. Typical stabilizers include for example sodium hydrogen sulfite, sodium sulfite, sodium thiosulfate, sodium pyrosulfite, and sodium metabisulfite. Chelating agents include for example sodium edetate and sodium citrate. Solubilizing agents include for example sterilized distilled water, distilled water for injections, and distilled water. Additionally, other useful components include for example anti-inflammatory agents, anti-allergic agents, antimicrobial agents, antibiotics, vitamins, and agents for promoting the cure of corneal injury.

The dose of indole derivative I, or a salt or solvate thereof as an active ingredient varies depending on the sex, age, body weight of a patient and the severity of the symptoms of the diseases. For eye drops, however, a formulation containing indole derivative I within the range of 0.0003 to 1 w/v %, preferably 0.001 to 0.5 w/v % can be applied topically once or twice daily. For injection, a formulation containing indole derivative I within the range of 0.0003 to 1 w/v % by weight, preferably 0.001 to 0.5 w/v % by weight can be applied once or twice daily.

To prepare the formulation of the present invention, indole derivative I and the photostabilizer selected are appropriately blended, if desired, together with isotonic agents, pH adjusting agents, preservatives, thickeners, auxiliary solubilizing agents, typical stabilizers, chelating agents, solubilizing agents and other useful components according to conventional methods, and then the preparation is filled in an appropriate sterilized container. The container can be those commonly used in the art depending on the type of the pharmaceutical formulation. In order to prevent the adsorption of indole derivative I, plastic containers made of for example Teflon, silicon, polypropylene, polystyrene, polyethylene, polyethylene terephthalate and polyethylene naphthalate are suitable. From the respect of handling and adsorptivity, containers made of polypropylene, polyethylene, polyethylene terephthalate and polyethylene naphthalate are preferable. Containers may be transparent, semi-transparent or appropriately colored.

The present invention is further illustrated by the following examples, but is not restricted by these examples in any way.

EXAMPLES 1 to 15

Aqueous Liquid Formulations Comprising Indole Derivative

Compound 1 (in formula I, R=ethyl group; Y=pivaloyloxy group) or compound 2 (in formula I, R=2,2,2-trifluoroethyl group; Y=pivaloyloxy group) shown in Table 1 and the components as shown in Table 2 were dissolved together in sterile distilled water in each Example, and the solutions were adjusted to 100 mL in total volume. If necessary, appropriate quantities of 1N sodium hydroxide and dilute hydrochloric acid were added to adjust the solutions to intended pH. The resulting aqueous solutions were aseptically filtered in aseptic environment, and the filtrates were filled into eye-drop containers rinsed and sterilized, to prepare colorless and clear aqueous liquid formulations.

TABLE 2(1)

| | Example No. | | | | | | | |
|---|---|---|---|---|---|---|---|---|
| | 1 | 2 | 3 | 4 | 5 | 6 | 7 | 8 |
| Compound 1 | 30 | 30 | 30 | 100 | 100 | 100 | 100 | 100 |
| Compound 2 | | | | | | | | |
| Boric acid | 1500 | | 1000 | 1500 | | 1000 | | |
| Borax | 10 | | | 10 | | | | |
| Sodium monohydrogen phosphate | | 360 | | | 360 | | 2150 | 1600 |
| Sodium dihydrogen phosphate | | 1400 | | | 1400 | | 630 | |
| Sodium hydrogen carbonate | | | 10 | | | 10 | | |
| Sodium chloride | 130 | 320 | 400 | 130 | 320 | 400 | 250 | 350 |
| Polysorbate 80 | | | | | | | 200 | |
| Benzalkonium chloride | 3 | 3 | 3 | 10 | 3 | 3 | 5 | 10 |
| Dilute hydrochloric acid | q.s. | q.s. | q.s. | q.s. | q.s. | q.s. | q.s. | q.s. |
| 1 N Sodium hydroxide | q.s. | q.s. | q.s. | q.s. | q.s. | q.s. | q.s. | q.s. |
| pH | 6.0 | 6.0 | 6.0 | 6.0 | 6.0 | 6.0 | 7.0 | 5.0 |
| Osmotic pressure ratio | 1.0 | 1.0 | 1.0 | 1.0 | 1.0 | 1.0 | 1.0 | 1.0 |

TABLE 2(2)

| | Example No. | | | | | | |
|---|---|---|---|---|---|---|---|
| | 9 | 10 | 11 | 12 | 13 | 14 | 15 |
| Compound 1 | 30 | 1 | 500 | | 30 | 30 | 30 |
| Compound 2 | | | | 30 | | | |
| Boric acid | 1500 | 1500 | 1500 | 1500 | 1470 | | 1000 |
| Borax | 10 | 10 | 10 | 10 | 10 | | |
| Sodium monohydrogen phosphate | | | | | | 360 | |
| Sodium dihydrogen phosphate | | | | | | 1400 | |
| Sodium hydrogen carbonate | | | | | | | 10 |
| Sodium chloride | 130 | 130 | 130 | 130 | 130 | 320 | 400 |
| Polysorbate 80 | | | | | | | |
| Benzalkonium chloride | 1 | 3 | 3 | 3 | | | |
| Dilute hydrochloric acid | q.s. | q.s. | q.s. | q.s. | q.s. | q.s. | q.s. |
| 1 N Sodium hydroxide | q.s. | q.s. | q.s. | q.s. | q.s. | q.s. | q.s. |
| pH | 6.0 | 6.0 | 6.0 | 6.0 | 6.0 | 6.0 | 6.0 |
| Osmotic pressure ratio | 1.0 | 1.0 | 1.0 | 1.0 | 1.0 | 1.0 | 1.0 |

Note: The components are shown in unit mg/100 mL.

The formulations were subjected to the photostability test by the method of Test Example. Consequently, it was found that all the formulations were excellent in terms of photostability.

Test Example 1

Photostability Test

1. Method

Five mL of a test sample in aqueous solution was charged in a colorless transparent glass ampoule (occluded glass ampoule), a colorless plastic eye-drop container (polyethylene nozzle-equipped polyethylene-made colorless plastic eye-drop container with a screw-in polyethylene cap) or a quartz Meyer (colorless quartz Meyer sealed with quartz stopper).

Under the following conditions, photoirradiation amounting in total to 400,000 lux.hr from white fluorescent lamp was done on the individual samples. The content of compound 1 in each of the samples prior to photoirradiation (immediately after preparation) and after photoirradiation was measured by high-performance liquid chromatography.

Conditions for photoirradiation
Apparatus used: photostable test apparatus (double-inversion type) (LT-120D3CJ; manufactured by

NAGANO SCIENTIFIC EQUIPMENT MFG. CO., LTD.).

| Light source used | : | D65 fluorescent lamp |
|---|---|---|
| Test conditions | : | 25° C., 5000 lux |
| Photoinadiation time | : | 80 hours (continuos) |
| Total illumination intensity | : | 400,000 lux · hr |

The aforementioned photoirradiation conditions correspond to daily 8-hr photoirradiation for four months at an illumination intensity of 500 lux at the rate of 25 days per month. In-hospital illumination intensity is usually 500 to 1,000 lux.

Conditions for high-performance liquid chromatography

Column: Inertsil ODS-3, 5 μm, 4.6-mm inner diameter× 25-cm length
Column temperature: 25° C.
Mobile phase: 0.02M phosphate buffer, pH 3.0/ acetonitrile mix solution (3:2)
Flow volume: 1.0 mL/min
Wavelength for detection: UV 225 nm
The residual ratio of the compound was determined by the calculation equation:

The residual ratio of compound 1(%)=(content of compound 1 after treatment with photoirradiation in sample)/(content of compound 1 prior to the treatment in sample)×100

Assessment criteria of photostability was that sample with a residual ratio exceeding 85% was marked with double circle, and sample with a residual ratio of less than 85% was marked with ×. Pharmaceutical formulations to be maintained by patients such as eye drops among pharmaceutical products should be designed to be stable securely for one month or longer, after the formulations are handed over to patients. When the photostability reaches a residual ratio at 85% or more as assessed by the method described above, the residual amount of the active ingredient reaches 95% or more as calculated a month later by interpolation. In such case, it can be determined that the active ingredient still remains in an amount capable of substantially exerting the therapeutic effect.

2. Stability in Glass Container

According to the method described in the item 1, 5 mL each of the aqueous liquid formulations of Examples 1 to 3 and 13 to 15 (free of antiseptics)and 5 mL each of the formulations of Comparative Examples 1 and 2 prepared similarly from the components shown in Table 3 were individually placed into colorless, transparent glass ampoules (occluded glass ampoules), for testing the photostability. The results are shown in Table 3.

TABLE 3

Photostability test of indole derivative-containing aqueous liquid formulations (glass)

| Blend ingredient (mg/100 mL) | Ex. 1 | Ex. 2 | Ex. 3 | Ex. 13 | Ex. 14 | Ex. 15 | Comparative Ex. 1 | Comparative Ex. 2 |
|---|---|---|---|---|---|---|---|---|
| Container material | glass | glass | glass | glass | glass | glass | glass | glass |
| Compound 1 | 30 | 30 | 30 | 30 | 30 | 30 | 30 | 30 |
| Boric acid | 1500 | | 1000 | 1470 | | 1000 | | |
| Borax | 10 | | | 10 | | | | |
| Sodium monohydrogen phosphate | | 360 | | | 360 | | | |
| Sodium dihydrogen phosphate | | 1400 | | | 1400 | | | |
| Sodium hydrogen carbonate | | | 10 | | | 10 | | |
| Citric acid | | | | | | | 140 | 140 |
| Sodium citrate | | | | | | | 1260 | 1260 |
| Sodium chloride | 130 | 320 | 400 | 130 | 320 | 400 | 500 | 500 |
| Benzalkonium chloride | 3 | 3 | 3 | | | | 3 | |
| Dilute hydrochloric acid | q.s. | q.s. | q.s. | q.s. | q.s. | q.s. | q.s. | q.s. |
| 1 N Sodium hydroxide | q.s. | q.s | q.s. | q.s. | q.s. | q.s. | q.s. | q.s. |
| pH | 6.0 | 6.0 | 6.0 | 6.0 | 6.0 | 6.0 | 6.0 | 6.0 |
| Osmotic pressure ratio | 1.0 | 1.0 | 1.0 | 1.0 | 1.0 | 1.0 | 1.0 | 1.0 |
| Appearance after photoirradiation | Colorless, clear | colorless, clear | colorless, clear | colorless, clear | colorless, clear | colorless, clear | colorless, clear | colorless, clear |
| Residual ratio (%) of compound 1 | 90.2 | 85.9 | 87.1 | 96.3 | 92.6 | 92.6 | 80.5 | 80.1 |
| Photostability | Double circle | Double circle | Double circle | Double circle | Double circle | Double circle | x | x |

In this test, the residual ratios were almost 100%, when the exterior of the container was optically shielded with aluminium prior to photoirradiation. No adsorption of compound 1 on the containers was observed during storage.

Table 3 shows that the stability of the compound 1 was enhanced in the aqueous liquid formulations of the present invention than in the formulations of Comparative Examples 1 and 2.

3. Stability in Plastic or Quartz Containers

According to the method described above, 5 mL each of the aqueous liquid formulations of Examples 1 to 5 and 13 to 15 (free of antiseptics) was placed in a colorless, plastic eye-drop containers(polyethylene nozzle-equipped colorless polyethylene plastic eye-drop container with screw-in polyethylene caps) or a quartz Meyer (colorless quartz Meyer sealed with quartz stopper), for testing the photostability. The results are shown in Table 4.

TABLE 4

Photostability test of indole derivative-containing aqueous liquid formulations (plastic or quartz)

| | Ex. 1 | Ex. 2 | Ex. 3 | Ex. 4 | Ex. 5 | Ex. 13 | Ex. 14 | Ex. 15 |
|---|---|---|---|---|---|---|---|---|
| Container material | plast-ic | plast-ic | plast-ic | plast-ic | quartz | plast-ic | plast-ic | plast-ic |
| Appearance after photoirradiation | colorless, clear | colorless, clear | colorless, clear | colorless, clear | colorless, clear | colorless, clear | colorless, clear | colorless, clear |
| Residual ratio (%) of compound 1 | 94.1 | 91.4 | 92.8 | 90.4 | 87.1 | 96.5 | 93.7 | 94.5 |
| Photostability | double circle | double circle | double circle | double circle | double circle | double circle | double circle | double circle |

In this test, the residual ratios were almost 100%, when the exteriors of the containers were optically shielded with aluminium prior to photoirradiation. No adsorption of compound 1 on the containers was observed during storage.

Table 4 shows that compound 1 is stable against light in the aqueous liquid formulations containing boric acid, borax, phosphate salts and/or carbonate salts in accordance with the present invention. Additionally, the formulations of Examples 13 to 15, which are free of an antiseptic benzalkonium chloride, were also stable, while the residual ratios of compound 1 were above 85% in the aqueous solutions. The results in Tables 3 and 4 show that the photostability is higher in the plastic container than in the glass container.

The above test was carried out using compound 1, but the results apparently are also true in other indole derivatives of formula I.

INDUSTRIAL APPLICABILITY

The aqueous liquid formulation containing indole derivative I and one or more photostabilizers selected from boric acid, borax, phosphate salts and carbonate salts in accordance with the present invention prominently enhance the photostability of a compound that is readily decomposable under exposure to light in aqueous solution. Therefore, the formulations can allow active ingredients to sufficiently exert the pharmacological action for a long term from the stage of pharmaceutical preparation to the stage when patients terminate the use. Thus, the formulations can allow the clinical application of indole derivative I, and can make contributions for example to the promotion of the therapeutic treatment of diseases with high intraocular tension and glaucoma. Additionally because the formulations can be used to prepare an eye drop with low eye irritation using a minimum amount of photostabilizers, the eye drop is safe over long-term dosing. Thus, the eye drop can easily ensure patient compliance and readily achieve the therapeutic effect. Further, the present invention avoids use of light-shielding treatment such as the use of colored container. Thus, advantageously, the aqueous liquid formulations are easily handleable by not only manufacturers but also users.

What is claimed is:

1. An aqueous liquid formulation which consists essentially of a compound of formula I:

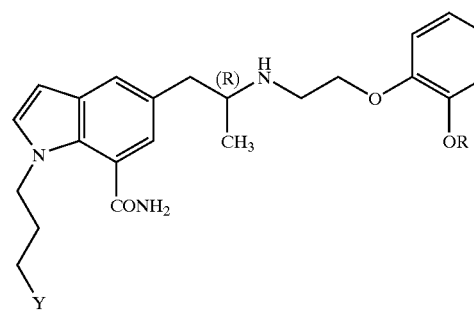

wherein Y is a hydroxy group, a carboxyl group, an acyloxy group or an alkoxycarbonyl group; and R is a lower alkyl group or a lower alkyl group with one or more halogen atoms; or a pharmaceutically acceptable salt thereof or a pharmaceutically acceptable solvate thereof as an active ingredient, together with boric acid, borax, a phosphate salt, or carbonate salt wherein the photostability of the active ingredient in the aqueous liquid formulation is enhanced compared to an identical aqueous liquid formulation without boric acid, borax, a phosphate salt, or carbonate salt.

2. The aqueous liquid formulation according to claim 1, in which the formulation consists essentially of a compound of formula I, wherein Y is a hydroxy group or an acyloxy group; and R is a methyl group, an ethyl group, a propyl group, an isopropyl group or a trifluoroethyl group; or a pharmaceutically acceptable salt thereof or a pharmaceutically acceptable solvate thereof as an active ingredient.

3. The aqueous liquid formulation according to claim 1, in which the formulation consists essentially of a compound of formula I, wherein Y is a hydroxy group or a pivaloyloxy group; and R is an ethyl group or a trifluoroethyl group; or a pharmaceutically acceptable salt thereof or a pharmaceutically acceptable solvate thereof as an active ingredient.

4. The aqueous liquid formulation according to claim 1, in which the formulation comprises a compound of formula I, or a pharmaceutically acceptable salt thereof or a pharmaceutically acceptable solvate of them as an active ingredient, together with one or more substances selected from the group consisting of boric acid, borax and phosphate salts.

5. The aqueous liquid formulation according to claim 1, in which the formulation comprises a compound of formula I, a pharmaceutically acceptable salt thereof or a pharmaceutically acceptable solvate of them as an active ingredient, together with boric acid and/or borax.

6. A process for producing an aqueous liquid formulation, which consists essentially of blending a compound of formula I:

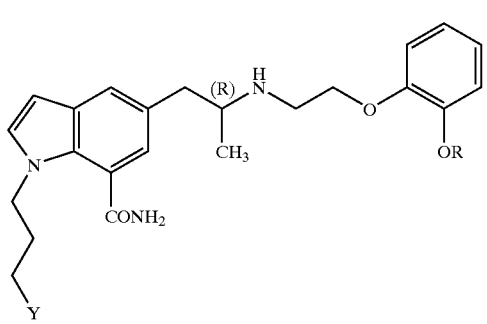

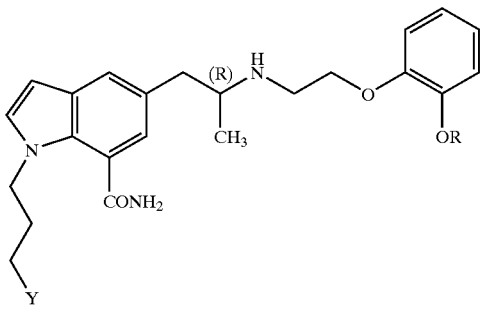

wherein Y is a hydroxy group, a carboxyl group, an acyloxy group or an alkoxycarbonyl group; and R is a lower alkyl group or a lower alkyl group with one or more halogen atoms, a pharmaceutically acceptable salt thereof or a pharmaceutically acceptable solvate thereof as an active ingredient together with boric acid, borax, a phosphate salts, or carbonate salt, wherein the photostability of the active ingredient in the aqueous liquid formulation is enhanced compared to an identical aqueous liquid formulation without boric acid, borax, a phosphate salt, or carbonate salt.

7. A method for photostabilizing an active ingredient in an aqueous liquid formulation wherein the active ingredient is a compound of formula I;

wherein Y is a hydroxy group, a carboxyl group, an acyloxy group or an alkoxycarbonyl group; and R is a lower alkyl group or a lower alkyl group with one or more halogen atoms, or a pharmaceutically acceptable salt thereof or a pharmaceutically acceptable solvate thereof which consists essentially of incorporating into the formulation boric acid, borax, a phosphate salt, or carbonate salt.

\* \* \* \* \*